(12) United States Patent
Lu

(10) Patent No.: US 9,370,601 B2
(45) Date of Patent: *Jun. 21, 2016

(54) DEXTRAN-BASED POLYMER TISSUE ADHESIVE FOR MEDICAL USE

(71) Applicant: Actamax Surgical Materials, LLC, Berkeley, CA (US)

(72) Inventor: Helen S. M. Lu, Wallingford, PA (US)

(73) Assignee: Actamax Surgical Materials, LLC, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/465,037

(22) Filed: Aug. 21, 2014

(65) Prior Publication Data

US 2015/0105346 A1   Apr. 16, 2015

Related U.S. Application Data

(63) Continuation of application No. 12/742,439, filed as application No. PCT/US2008/083545 on Nov. 14, 2008, now Pat. No. 8,846,095.

(60) Provisional application No. 61/003,060, filed on Nov. 14, 2007.

(51) Int. Cl.
*A61L 24/08* (2006.01)
*A61L 24/00* (2006.01)

(52) U.S. Cl.
CPC .............. *A61L 24/08* (2013.01); *A61L 24/0031* (2013.01)

(58) Field of Classification Search
None
See application file for complete search history.

(56) References Cited

U.S. PATENT DOCUMENTS

| 4,584,188 | A | 4/1986 | Graham |
|---|---|---|---|
| 5,112,618 | A | 5/1992 | Cartmell et al. |
| 5,116,824 | A | 5/1992 | Miyata et al. |
| 5,162,430 | A | 11/1992 | Rhee et al. |
| 5,292,802 | A | 3/1994 | Rhee et al. |
| 5,308,889 | A | 5/1994 | Rhee et al. |
| 5,324,775 | A | 6/1994 | Rhee et al. |
| 5,328,995 | A | 7/1994 | Schaulin et al. |
| 5,505,952 | A | 4/1996 | Jiang et al. |
| 5,514,379 | A | 5/1996 | Weissleder et al. |
| 5,643,575 | A | 7/1997 | Martinez et al. |
| 5,733,563 | A | 3/1998 | Fortier |
| 7,179,660 | B1 | 2/2007 | Kirakossian et al. |
| 8,846,095 | B2 | 9/2014 | Lu |
| 2005/0002893 | A1 | 1/2005 | Goldmann |
| 2006/0078536 | A1 | 4/2006 | Kodokian et al. |
| 2006/0292030 | A1 | 12/2006 | Odermatt et al. |
| 2008/0021563 | A1 | 1/2008 | Chudzik |
| 2008/0069857 | A1 | 3/2008 | Yeo et al. |

FOREIGN PATENT DOCUMENTS

| JP | 1980180243 | 12/1980 |
|---|---|---|
| JP | 1986146037 | 6/1986 |
| WO | WO-9115368 A1 | 10/1991 |
| WO | WO-9901143 A1 | 1/1999 |
| WO | WO-2009064963 A2 | 5/2009 |

OTHER PUBLICATIONS

Pfannemuller, B., et al., "Chemical Modification of the Surface of the Starch Granules", Starch/Starke, vol. 95, No. 9, 1983, pp. 298-303.
Letter from European patent attorney D.P. Matthews of Dehns regarding the European equivalent of Application No. 08849908.2 of current U.S. Appl. No. 12/742,439 (EPO Response) dated May 1, 2012.

*Primary Examiner* — David J Blanchard
*Assistant Examiner* — Garen Gotfredson
(74) *Attorney, Agent, or Firm* — McCarter & English, LLP

(57) ABSTRACT

A tissue adhesive formed by reacting an aminodextran containing primary amine groups with an oxidized dextran containing aldehyde groups is described. The dextran-based polymer tissue adhesive is particularly useful in medical applications where low swell and slow degradation are needed, for example sealing the dura, ophthalmic procedures, tissue repair, antiadhesive applications, drug delivery, and as a plug to seal a fistula or the punctum.

12 Claims, No Drawings

DEXTRAN-BASED POLYMER TISSUE ADHESIVE FOR MEDICAL USE

CROSS-REFERENCE TO RELATED APPLICATION

This application is a Continuation of U.S. patent application Ser. No. 12/742,439, filed May 12, 2010, which is incorporated herein by reference and which is a U.S. National Stage application filed under 35 U.S.C. Section 371 of PCT/US2008/83545, filed Nov. 14, 2008, which claims priority of U.S. Provisional Application Ser. No. 61/003,060, filed Nov. 14, 2007.

FIELD OF THE INVENTION

The invention relates to the field of medical adhesives. More specifically, the invention relates to a polymer tissue adhesive formed by reacting an aminodextran containing primary amine groups with an oxidized dextran containing aldehyde groups.

BACKGROUND OF THE INVENTION

Tissue adhesives have many potential medical applications, including wound closure, supplementing or replacing sutures or staples in internal surgical procedures, adhesion of synthetic onlays or inlays to the cornea, drug delivery devices, and as anti-adhesion barriers to prevent post-surgical adhesions. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, the Fibrin-based adhesives do not covalently bind to the underlying tissue.

Several types of hydrogel tissue adhesives have been developed which have improved adhesive and cohesive properties and are nontoxic. These hydrogels are generally formed by reacting a component having nucleophilic groups with a component having electrophilic groups capable of reacting with the nucleophilic groups of the first component to form a crosslinked network via covalent bonding. However, these hydrogels typically swell or dissolve away too quickly, or lack sufficient adhesion or mechanical strength, thereby decreasing their effectiveness as surgical adhesives.

Kodokian et al. (copending and commonly owned U.S. Patent Application Publication No. 2006/0078536) describe hydrogel tissue adhesives formed by reacting an oxidized polysaccharide with a water-dispersible, multi-arm polyether amine. These adhesives provide improved adhesion and cohesion properties, crosslink readily at body temperature, maintain dimensional stability initially, do not degrade rapidly, and are nontoxic to cells and non-inflammatory to tissue. Hydrogel tissue adhesives with low swell and slow degradation are needed for applications including but not limited to, sealing the dura, ophthalmic procedures, tissue repair, anti-adhesive applications, drug delivery, and sealing a fistula or the punctum.

Polysaccharide-based hydrogels are known and various uses have been described, for example, use as a drug carrier (Spiro et al., WO 99/01143), use as a coating on a carrier for use in diagnostic or therapeutic methods (Kirakossian et al., U.S. Pat. No. 7,179,660), and use as a coating for prohibiting post surgical adhesions (Yeo et al., U.S. Patent Application Publication No. 2008/0069857). Additionally, a polysaccharide-based hydrogel formed by reacting oxidized dextran and chitosan for use as a tissue adhesive is described by Goldmann (U.S. Patent Application Publication No. 2005/0002893) and Odermatt et al. (U.S. Patent Application Publication No. 2006/0292030).

Consequently, the problem to be solved is to provide a tissue adhesive material with low swell and a slow degradation rate for use in surgical procedures as well as other medical applications. The stated problem is addressed herein by the discovery that hydrogels formed by the reaction of an aminodextran containing primary amine groups and an oxidized dextran containing aldehyde groups possess these desired properties.

SUMMARY OF THE INVENTION

An embodiment provides a kit comprising:
a) at least one dextran that has been derivatized to provide at least one aminodextran that contains primary amine groups, said at least one dextran having a weight-average molecular weight of about 1,000 to about 1,000,000 Daltons, said at least one aminodextran having an amine substitution level of about 5% to about 65%; and
b) at least one dextran that has been oxidized to provide at least one oxidized dextran containing aldehyde groups, said at least one dextran having a weight-average molecular weight of about 1,000 to about 1,000,000 Daltons, said at least one oxidized dextran having an equivalent weight per aldehyde group of about 65 to about 1500 Daltons;
wherein the at least one aminodextran and the at least one oxidized dextran are unreacted.

Another embodiment provides the kit, wherein the aminodextran is a first aqueous solution or dispersion and the oxidized dextran a second aqueous solution or dispersion.

Another embodiment provides the, wherein the first aqueous solution or dispersion contains the aminodextran at a concentration of about 5% to about 70% by weight relative to the total weight of the solution or dispersion.

Another embodiment provides the kit, wherein the second aqueous solution or dispersion contains the oxidized dextran at a concentration of about 5% to about 50% by weight relative to the total weight of the solution or dispersion.

In yet another embodiment, the kit wherein the aminodextran and the oxidized dextran are finely divided powders.

In yet another embodiment, the kit wherein the equivalent weight per aldehyde group of the oxidized dextran is about 90 to about 1500 Daltons.

An embodiment provides a dried hydrogel product formed by a process comprising the steps of:
a) reacting in a solvent (i) at least one dextran that has been derivatized to provide at least one aminodextran that contains primary amine groups, said at least one dextran having a weight-average molecular weight of about 1,000 to about 1,000,000 Daltons, said at least one aminodextran having an amine substitution level of about 5% to about 65%; with (ii) at least one dextran that has been oxidized to provide at least one oxidized dextran containing aldehyde groups, said at least one dextran having a weight-average molecular weight of about 1,000 to about 1,000,000 Daltons, said at least one oxidized dextran having an equivalent weight per aldehyde group of about 65 to about 1500 Daltons, to form a hydrogel;
b) treating said hydrogel to remove at least a portion of said solvent to form the dried hydrogel.

Another embodiment provides the dried hydrogel, wherein said dried hydrogel is a film.

Another embodiment provides the dried hydrogel, wherein the process further comprises comminuting the dried hydrogel to form finely divided particles.

Another embodiment provides the dried hydrogel, wherein the equivalent weight per aldehyde group of the oxidized dextran is about 90 to about 1500 Daltons.

An embodiment provides a combination for use in coating an anatomical site comprising:
  a) at least one dextran that has been derivatized to provide at least one aminodextran that contains primary amine groups, said at least one dextran having a weight-average molecular weight of about 1,000 to about 1,000,000 Daltons, said at least one aminodextran having an amine substitution level of about 5% to about 65%; followed by
  b) at least one dextran that has been oxidized to provide at least one oxidized dextran containing aldehyde groups, said at least one dextran having a weight-average molecular weight of about 1,000 to about 1,000,000 Daltons, said at least one oxidized dextran having an equivalent weight per aldehyde group of about 65 to about 1500 Daltons; or alternatively (b) followed by (a).

Another embodiment provides the combination, wherein the aminodextran is a first aqueous solution or dispersion and the oxidized dextran is a second aqueous solution or dispersion.

Another embodiment provides the combination, wherein the first aqueous solution or dispersion contains the aminodextran at a concentration of about 5% to about 70% by weight relative to a total weight of the solution or dispersion.

In yet another embodiment, the combination, wherein the second aqueous solution or dispersion contains the oxidized dextran at a concentration of about 5% to about 50% by weight relative to the total weight of the solution or dispersion.

In yet another embodiment, the combination, wherein the aminodextran and the oxidized dextran are finely divided powders.

Another embodiment provides the combination, wherein the equivalent weight per aldehyde group of the oxidized dextran is about 90 to about 1500 Daltons.

An embodiment provides a method for applying a coating to an anatomical site on tissue of a living organism comprising:
applying to the site
  a) at least one dextran that has been derivatized to provide at least one aminodextran that contains primary amine groups, said at least one dextran having a weight-average molecular weight of about 1,000 to about 1,000,000 Daltons, said at least one aminodextran having an amine substitution level of about 5% to about 65%; followed by
  b) at least one dextran that has been oxidized to provide at least one oxidized dextran containing aldehyde groups, said at least one dextran having a weight-average molecular weight of about 1,000 to about 1,000,000 Daltons, said at least one oxidized dextran having an equivalent weight per aldehyde group of about 65 to about 1500 Daltons; or applying (b) followed by (a) and mixing (a) and (b) on the site; or premixing (a) and (b) and applying the resulting mixture to the site.

Another embodiment provides the method, wherein the aminodextran is in the form of a first aqueous solution or dispersion and the oxidized dextran is in the form of a second aqueous solution or dispersion.

Another embodiment provides the method, wherein the first aqueous solution or dispersion contains the aminodextran at a concentration of about 5% to about 70% by weight relative to the total weight of the solution or dispersion.

In yet another embodiment, the method, wherein the second aqueous solution or dispersion contains the oxidized dextran at a concentration of about 5% to about 50% by weight relative to the total weight of the solution or dispersion.

In yet another embodiment, the method, wherein the aminodextran and the oxidized dextran are in the form of finely divided powders.

In yet another embodiment, the method, wherein the equivalent weight per aldehyde group of the oxidized dextran is about 90 to about 1500 Daltons.

An embodiment provides a combination for use in bonding at least two anatomical sites together, wherein the combination is applied to at least one of the at least two anatomical sites, the combination comprising;
  a) at least one dextran that has been derivatized to provide at least one aminodextran that contains primary amine groups, said at least one dextran having a weight-average molecular weight of about 1,000 to about 1,000,000 Daltons, said at least one aminodextran having an amine substitution level of about 5% to about 65%; followed by
  b) at least one dextran that has been oxidized to provide at least one oxidized dextran containing aldehyde groups, said at least one dextran having a weight-average molecular weight of about 1,000 to about 1,000,000 Daltons, said at least one oxidized dextran having an equivalent weight per aldehyde group of about 65 to about 1500 Daltons; or alternatively (b) followed by (a).

Another embodiment provides the combination, wherein the aminodextran is a first aqueous solution or dispersion and the oxidized dextran is a second aqueous solution or dispersion.

Another embodiment provides the combination, wherein the first aqueous solution or dispersion contains the aminodextran at a concentration of about 5% to about 70% by weight relative to a total weight of the solution or dispersion.

In yet another embodiment, the combination, wherein the second aqueous solution or dispersion contains the oxidized dextran at a concentration of about 5% to about 50% by weight relative to the total weight of the solution or dispersion.

In yet another embodiment, the combination, wherein the at least one aminodextran and the at least one oxidized dextran are finely divided powders.

In yet another embodiment, the combination, wherein the equivalent weight per aldehyde group of the oxidized dextran is about 90 to about 1500 Daltons.

Another embodiment provides a product for use in a coating an anatomical site comprising the dried hydrogel.

Another embodiment provides the product, wherein said dried hydrogel is a film.

Another embodiment provides the product, wherein said dried hydrogel is finely divided particles.

An embodiment provides a method for bonding at least two anatomical sites together comprising:
applying to at least one of the at least two anatomical sites:
  a) at least one dextran that has been derivatized to provide at least one aminodextran that contains primary amine groups, said at least one dextran having a weight-average molecular weight of about 1,000 to about 1,000,000 Daltons, said at least one aminodextran having an amine substitution level of about 5% to about 65%; followed by
  b) at least one dextran that has been oxidized to provide at least one oxidized dextran containing aldehyde groups, said at least one dextran having a weight-average molecular weight of about 1,000 to about 1,000,000 Daltons, said at least one oxidized dextran having an equivalent weight per aldehyde group of about 65 to about 1500 Daltons; or alternatively, applying (b) followed by (a) and mixing (a) and (b) on the at least one site, or alternatively, premixing (a) and (b) and applying the resulting mixture to the at least one site; and contacting the at least two anatomical sites together.

Another embodiment provides the method, wherein the aminodextran is in the form of a first aqueous solution or dispersion and the oxidized dextran is in the form of a second aqueous solution or dispersion.

Another embodiment provides the method, wherein the first aqueous solution or dispersion contains the aminodextran at a concentration of about 5% to about 70% by weight relative to the total weight of the solution or dispersion.

In yet another embodiment, the method wherein the second aqueous solution or dispersion contains the oxidized dextran at a concentration of about 5% to about 50% by weight relative to the total weight of the solution or dispersion.

In yet another embodiment, the method wherein the at least one aminodextran and the at least one oxidized dextran are in the form of finely divided powders.

Another embodiment provides the method, wherein the equivalent weight per aldehyde group of the oxidized dextran is about 90 to about 1500 Daltons.

In yet another embodiment, a method for applying a coating to an anatomical site on tissue of a living organism comprising applying to the site the dried hydrogel.

In yet another embodiment, the method, wherein said dried hydrogel is in the form of a film.

In yet another embodiment, the method, wherein said dried hydrogel is in the form of finely divided particles.

DETAILED DESCRIPTION OF THE INVENTION

Disclosed herein is a polymer tissue adhesive formed by reacting at least one aminodextran containing primary amine groups and at least one oxidized dextran containing aldehyde groups. The dextran-based polymer tissue adhesive is particularly useful in medical applications where low swell and slow degradation are needed, for example sealing the dura, ophthalmic procedures, tissue repair, antiadhesive applications, drug delivery, and as a plug to seal a fistula or the punctum. Due to the positive charge on the aminodextran, the polymer tissue adhesive disclosed herein may possess antimicrobial properties and promote wound healing.

The following definitions are used herein and should be referred to for interpretation of the claims and the specification.

The term "oxidized dextran" refers to dextran that has been reacted with an oxidizing agent to introduce aldehyde groups into the molecule.

The terms "aminodextran" and "dextran amine" are used interchangeably herein to refer to dextran that has been derivatized (i.e., chemically modified) to contain primary amine groups.

The term "equivalent weight per aldehyde group" refers to the average molecular weight of the compound divided by the number of aldehyde groups in the molecule.

The term "amine substitution level" as used herein, refers to the percent of saccharide rings in dextran that are substituted with a primary amine group. The amine substitution level is determined using proton nuclear magnetic resonance (NMR) spectroscopy, as described herein.

The term "hydrogel" refers to a water-swellable polymeric matrix, consisting of a three-dimensional network of macromolecules held together by covalent or non-covalent crosslinks, that can absorb a substantial amount of water to form an elastic gel.

The term "crosslink" refers to a bond or chain of atoms attached between and linking two different polymer chains.

The term "dried hydrogel" refers to a hydrogel that has been treated to remove at least a portion of the solvent contained therein. Preferably, substantially all of the solvent is removed from the hydrogel.

The term "% by weight" as used herein refers to the weight percent relative to the total weight of the solution or dispersion, unless otherwise specified.

The term "anatomical site" refers to any external or internal part of the body of humans or animals.

The term "tissue" refers to any tissue, both living and dead, in humans or animals.

The term medical application is refers to medical applications as related to humans and animals.

The meaning of abbreviations used is as follows: "min" means minute(s), "h" means hour(s), "sec" means second(s), "d" means day(s), "mL" means milliliter(s), "L" means liter(s), "µL" means microliter(s), "cm" means centimeter(s), "mm" means millimeter(s), "µm" means micrometer(s), "mol" means mole(s), "mmol" means millimole(s), "g" means gram(s), "mg" means milligram(s), "wt %" means percent by weight, "mol %" means mole percent, "M" means molar concentration, "Vol" means volume, "v/v" means volume per volume, "Da" means Daltons, "kDa" means kiloDaltons, "mw" means molecular weight, "MWCO" means molecular weight cut-off, "kPa" means kilopascals, "$^1$H NMR" means proton nuclear magnetic resonance spectroscopy, "ppm" means parts per million, "PBS" means phosphate-buffered saline.

Dextrans

Dextran is a complex, branched polysaccharide that includes many glucose moieties joined together via glycosidic linkages to form straight chains. Dextrans having various average molecular weights are available from commercial sources such as Sigma-Aldrich (Milwaukee, Wis.) and Pharmacosmos A/S (Holbaek, Denmark). Typically, commercial preparations of dextran are a heterogeneous mixture having a distribution of different molecular weights, as well as a variable degree of branching, and are characterized by various molecular weight averages, for example, the weight-average molecular weight, or the number-average molecular weight, as is known in the art. Suitable dextrans have a weight-average molecular weight of about 1,000 to about 1,000,000 Daltons, preferably from about 3,000 to about 250,000 Daltons.

Oxidized Dextran Containing Aldehyde Groups

One reactant used to prepare the polymer tissue adhesive disclosed herein is an oxidized dextran containing aldehyde groups. Oxidized dextran may be prepared by oxidizing dextran using any suitable oxidizing agent, including but not limited to, periodates, hypochlorites, ozone, peroxides, hydroperoxides, persulfates, and percarbonates. In one embodiment, the dextran is oxidized by reaction with sodium periodate, for example as described by Mo et al. (*J. Biomater. Sci. Polymer Edn.* 11:341-351, 2000). The dextran may be reacted with different amounts of periodate to give dextrans with different degrees of oxidation and therefore, different amounts of aldehyde groups, as described in detail in the General Methods Section of the Examples herein. The aldehyde content of the oxidized dextran may be determined using methods known in the art. For example, the dialdehyde content of the oxidized dextran may be determined using the method described by Hofreiter et al. (*Anal Chem.* 27:1930-

1931, 1955), as described in detail in the General Methods Section of the Examples herein. In that method, the amount of alkali consumed per mole of dialdehyde in the oxidized dextran, under specific reaction conditions, is determined by a pH titration. The equivalent weight per aldehyde group of the oxidized dextran is about 65 to about 1500 Daltons, in addition about 90 to about 1500 Daltons.

In one embodiment, the oxidized dextran is prepared from dextran having a weight-average molecular weight of 8,500 to 11,500 Dalton, and has an equivalent weight per aldehyde group of about 146 Daltons.

In another embodiment, the oxidized dextran is prepared from dextran having a weight-average molecular weight of 8,500 to 11,500 Daltons and has an equivalent weight per aldehyde group of about 109 Daltons.

Aminodextran Containing Primary Amine Groups

The second reactant used to prepare the polymer tissue adhesive disclosed herein is aminodextran containing primary amine groups. Aminodextran containing primary amine groups can be prepared by chemical derivatization of dextran using methods known in the art. For example, dextran can be oxidized to produce oxidized dextran containing aldehyde groups, as described above. Then, the oxidized dextran can be reacted with a diamine, such as hexamethylene diamine, ethylene diamine, propylene diamine, and the like, to form Schiff base linkages. Optionally, the Schiff base linkages may be treated with a reducing agent such as sodium borohydride to form stable carbon-nitrogen bonds, as described in detail in the Examples herein. Aminodextran may also be prepared by reacting dextran with cyanogen bromide, followed by reaction with a diamine. Additionally, aminodextran can be prepared by the methods described by Kirakossian et al. (U.S. Pat. No. 7,179,660, Example A). The amine substitution level of the aminodextran is determined using proton NMR by determining the ratio of the integral of the peaks corresponding to the pendant amine-containing groups to the sum of the integrals of the peaks corresponding to the anomeric protons of the glucose ring and comparing it to the expected ratio for a fully derivatized product, as shown in the Examples herein.

In one embodiment, the amine substitution level of the aminodextran is from about 5% to about 65%.

In another embodiment, the aminodextran is prepared from dextran having a weight-average molecular weight of 8,500 to 11,500 Daltons and has an amine substitution level of about 46%.

In another embodiment, the aminodextran is prepared from dextran having a weight-average molecular weight of 60,000 to 90,000 Daltons and has an amine substitution level of about 32%.

In another embodiment, the aminodextran is prepared from dextran having a weight-average molecular weight of 400 to 500 kiloDaltons and has an amine substitution level of about 38%.

In another embodiment, the aminodextran is prepared from dextran having a weight-average molecular weight of about 2,000 kiloDaltons and has an amine substitution level of about 36%.

Methods of Using Dextran-Based Polymer Tissue Adhesive

The dextran-based polymer tissue adhesive disclosed herein may be used in various forms. In one embodiment, the oxidized dextran containing aldehyde groups and the aminodextran containing primary amine groups are used in the form of aqueous solutions or dispersions. Dispersion, as used herein, refers to a colloidal suspension capable of reacting with a second reactant in an aqueous medium. To prepare an aqueous solution or dispersion comprising aminodextran containing primary amine groups (referred to herein as the "first aqueous solution or dispersion"), at least one aminodextran is added to water to give a concentration of about 5% to about 70% by weight, in addition about 5% to about 50% by weight, in addition about 10% to about 50% by weight, and in addition about 10% to about 30% by weight, relative to the total weight of the solution or dispersion. Mixtures of different aminodextrans, having different average molecular weights and/or different equivalent weights per amine group, may also be used. If a mixture of different aminodextrans is used, the total concentration of the aminodextrans is about 5% to about 70% by weight, in addition about 5% to about 50% by weight, in addition about 10% to about 50% by weight, and in addition about 10% to about 30% by weight Similarly, to prepare an aqueous solution or dispersion comprising oxidized dextran containing aldehyde groups (referred to herein as the "second aqueous solution or dispersion"), at least one oxidized dextran is added to water to give a concentration of about 5% to about 50% by weight, in addition from about 10% to about 30% by weight, relative to the total weight of the solution or dispersion. Mixtures of different oxidized dextrans containing aldehyde groups, having different average molecular weights and/or different equivalent weights per aldehyde group, may also be used. If a mixture of different oxidized dextrans is used, the total concentration of the oxidized dextrans is about 5% to about 50% by weight, in addition about 10% to about 30% by weight, relative to the total weight of the solution or dispersion. The optimal concentrations of the two dextran solutions or dispersions to be used depends on the application, and can be readily determined by one skilled in the art using routine experimentation.

For use on living tissue, it is preferred that the aqueous solution or dispersion comprising the oxidized dextran(s) and the aqueous solution or dispersion comprising the aminodextran(s) be sterilized to prevent infection. Any suitable sterilization method known in the art that does not adversely affect the ability of the components to react to form an effective hydrogel may be used. For example the first aqueous solution or dispersion comprising at least one aminodextran may be sterilized using heat, ethylene oxide sterilization, ultra-violet radiation, or ultra-filtration through a 0.2 μm pore membrane. The second aqueous solution or dispersion comprising at least one oxidized dextran may be sterilized using heat, electron beam irradiation, gamma irradiation, ethylene oxide sterilization, ultra-violet radiation, or ultra-filtration through a 0.2 μm pore membrane.

The first aqueous solution or dispersion comprising the aminodextran(s) and/or the second aqueous solution or dispersion comprising the oxidized dextran(s) may further comprise various additives depending on the intended application. Preferably, the additive is compatible with the dextran. Specifically, the additive does not contain groups that would interfere with effective gelation of the hydrogel. The amount of the additive used depends on the particular application and may be readily determined by one skilled in the art using routine experimentation. For example, the first aqueous solution or dispersion and/or the second aqueous solution or dispersion may comprise at least one additive selected from pH modifiers, viscosity modifiers, antimicrobials, colorants, surfactants, pharmaceutical drugs and therapeutic agents.

The aqueous solution(s) or dispersion(s) may optionally include at least one pH modifier to adjust the pH of the solution(s). Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, nitrogen-containing compounds other than primary and secondary amines, and basic carbonates and phosphates.

The aqueous solution(s) or dispersion(s) may optionally include at least one thickener. The thickener may be selected from among known viscosity modifiers, including, but not limited to, polysaccharides and derivatives thereof, such as starch or hydroxyethyl cellulose.

The aqueous solution(s) or dispersion(s) may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate.

The aqueous solution(s) or dispersion(s) may also optionally include at least one colorant to enhance the visibility of the solution(s). Suitable colorants include dyes, pigments, and natural coloring agents. Examples of suitable colorants include, but are not limited to, FD&C and D&C colorants, such as FD&C Violet No. 2, FD&C Blue No. 1, D&C Green No. 6, D&C Green No. 5, D&C Violet No. 2; and natural colorants such as beetroot red, canthaxanthin, chlorophyll, eosin, saffron, and carmine.

The aqueous solution(s) or dispersion(s) may also optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

Additionally, the aqueous solution(s) or dispersion(s) may optionally include at least one pharmaceutical drug or therapeutic agent. Suitable drugs and therapeutic agents are well known in the art (for example see the United States Pharmacopeia (USP), *Physician's Desk Reference* (Thomson Publishing), *The Merck Manual of Diagnosis and Therapy* 18th ed., Mark H. Beers and Robert Berkow (eds.), Merck Publishing Group, 2006; or, in the case of animals, *The Merck Veterinary Manual*, 9th ed., Kahn, C. A. (ed.), Merck Publishing Group, 2005). Nonlimiting examples include, but are not limited to, anti-inflammatory agents, for example, glucocorticoids such as prednisone, dexamethasone, budesonide; non-steroidal anti-inflammatory agents such as indomethacin, salicylic acid acetate, ibuprofen, sulindac, piroxicam, and naproxen; fibrinolytic agents such as a tissue plasminogen activator and streptokinase; anti-coagulants such as heparin, hirudin, ancrod, dicumarol, sincumar, iloprost, L-arginine, dipyramidole and other platelet function inhibitors; antibodies; nucleic acids; peptides; hormones; growth factors; cytokines; chemokines; clotting factors; endogenous clotting inhibitors; antibacterial agents; antiviral agents; antifungal agents; anti-cancer agents; cell adhesion inhibitors; healing promoters; vaccines; thrombogenic agents, such as thrombin, fibrinogen, homocysteine, and estramustine; radio-opaque compounds, such as barium sulfate and gold particles and radiolabels.

The first aqueous solution or dispersion comprising the aminodextran(s) and the second aqueous solution or dispersion comprising the oxidized dextran(s) may be applied to an anatomical site on tissue of a living organism in any number of ways. Once both solutions or dispersions are applied to a site, they crosslink to form a hydrogel, a process referred to herein as curing, typically in about 2 seconds to about 2 minutes.

In one embodiment, the two aqueous solutions or dispersions are applied to the site sequentially using any suitable means including, but not limited to, spraying, brushing with a cotton swab or brush, or extrusion using a pipette, or a syringe. The solutions or dispersions may be applied in any order. Then, the solutions or dispersions are mixed on the site using any suitable device, such as a cotton swab, a spatula, or the tip of the pipette or syringe.

In another embodiment, the two aqueous solutions or dispersions are mixed manually before application to the site. The resulting mixture is then applied to the site before it completely cures using a suitable applicator, as described above.

In another embodiment, the two aqueous solutions or dispersions are contained in separate barrels of a double-barrel syringe. In this way the two aqueous solutions or dispersions are applied simultaneously to the site with the syringe. Suitable double-barrel syringe applicators are known in the art. For example, Redl describes several suitable applicators for use in the invention in U.S. Pat. No. 6,620,125, (particularly FIGS. 1, 5, and 6, which are described in Columns 4, line 10 through column 6, line 47). Additionally, the double barrel syringe may contain a motionless mixer, such as that available from ConProtec, Inc. (Salem, N.H.) or Mixpac Systems AG (Rotkreuz, Switzerland), at the tip to effect mixing of the two aqueous solutions or dispersions prior to application. Alternatively, the mixing tip may be equipped with a spray head, such as that described by Cruise et al. in U.S. Pat. No. 6,458,147. Additionally, the mixture of the two aqueous solutions or dispersions from the double-barrel syringe may be applied to the site using a catheter or endoscope. Devices for mixing a two liquid component tissue adhesive and delivering the resulting mixture endoscopically are known in the art and may be adapted for the mixing and delivery of the two aqueous solutions or dispersions disclosed herein (see for example, Nielson, U.S. Pat. No. 6,723,067; and Redl et al., U.S. Pat. No. 4,631,055). Suitable delivery devices for use in ophthalmic applications, where small volumes of the two aqueous solutions or dispersions or the mixture thereof are required, are also known in the art (see for example Miller et al., U.S. Pat. No. 4,874,368, and copending and commonly owned U.S. Patent Application No. 61/002,071).

In another embodiment, the first aqueous solution or dispersion and the second aqueous solution or dispersion are applied to the site simultaneously where they mix to form a hydrogel. The two aqueous solutions or dispersions may be applied to the site in various ways, for example, using a dual-lumen catheter, such as those available from Bistech, Inc. (Woburn, Mass.). Additionally, injection devices for introducing two liquid components endoscopically into the body simultaneously are known in the art and may be adapted for the delivery of the two aqueous solutions or dispersions disclosed herein (see for example, Linder et al., U.S. Pat. No. 5,322,510).

In another embodiment, the two aqueous solutions or dispersions may be applied to the site using a spray device, such as those described by Fukunaga et al. (U.S. Pat. No. 5,582,596), Delmotte et al. (U.S. Pat. No. 5,989,215) or Sawhney (U.S. Pat. No. 6,179,862).

In another embodiment, the two aqueous solutions or dispersions may be applied to the site using a minimally invasive surgical applicator, such as those described by Sawhney (U.S. Pat. No. 7,347,850).

In another embodiment, the tissue adhesive disclosed herein is used to bond at least two anatomical sites together. In this embodiment, the aqueous solution or dispersion comprising the oxidized dextran(s) is applied to at least one anatomical site, and the aqueous solution or dispersion comprising the aminodextran(s) is applied to at least one of either the same site or one other site. The two or more sites are contacted and held together manually or using some other means, such as a surgical clamp, for a time sufficient for the mixture to cure, typically from about 2 seconds to about 2 minutes. Alternatively, a mixture of the two aqueous solutions or dispersions either premixed manually or using a double-barrel syringe applicator, is applied to at least one of the anatomical sites to be bonded. The two or more sites are contacted and held together manually or using some other means, such as a surgical clamp, for a time sufficient for the mixture to cure.

In another embodiment, the oxidized dextran and the aminodextran are used in the form of finely divided powders. The powders may be prepared using any suitable method. For example, the aqueous solutions described above may be dried using heat, vacuum, a combination of heat and vacuum, or by lyophilization, to form powders. Optionally, the powders may be comminuted into finer particles using methods known in the art including, but not limited to, grinding, milling, or crushing with a mortar and pestle. The finely divided powders may be sterilized using the methods described above. The finely divided powders may be applied to an anatomical site on tissue of a living organism in a variety of ways. For example, the powders may be individually applied to the site in any order by sprinkling or spraying. Additionally, the two powders may be premixed and the resulting mixture applied to the site using the methods described above. The powders may be hydrated on the site by the addition of a suitable buffer (e.g., phosphate-buffered saline) or by the physiological fluids present at the site. The finely divided powders may also be used to bond two anatomical sites together as described above for the aqueous solutions or dispersions.

In another embodiment, the dextran-based polymer tissue adhesive disclosed herein is used in the form of a dried hydrogel. In this embodiment, a hydrogel is prepared by mixing a solution or dispersion comprising at least one oxidized dextran with a solution or dispersion comprising at least one aminodextran to form a hydrogel. The solutions or dispersions may be prepared in any suitable solvent, including but not limited to, water, ethanol, isopropanol, tetrahydrofuran, hexanes, polyethylene glycol, and mixtures thereof. If a mixture of solvents is used, it is preferable to use solvents that are miscible with each other. In one embodiment, the solvent is water. The solutions or dispersions may further comprise various additives depending on the intended application. Any of the additives described above may be used. The hydrogel is then treated to remove at least a portion of the solvent contained therein to form the dried hydrogel. Preferably, substantially all of the solvent is removed from the hydrogel. The solvent may be removed from the hydrogel using methods known in the art, for example, using heat, vacuum, a combination of heat and vacuum, or flowing a stream of dry air or a dry inert gas such as nitrogen over the hydrogel. The dried hydrogel may be sterilized using the methods described above. The dried hydrogel may be applied to an anatomical site in a number of ways, as described below. The dried hydrogel may be hydrated on the site by the addition of a suitable buffer (e.g., phosphate-buffered saline) or by the physiological fluids present at the site.

In one embodiment, the dried hydrogel is used in the form of a film. The dried hydrogel film may be formed by casting a mixture of the aqueous solutions or dispersions on a suitable substrate and treating the resulting hydrogel to form a dried hydrogel film. The dried hydrogel film may be applied directly to an anatomical site. Additionally, the dried hydrogel film may be used to bond two anatomical sites together.

In another embodiment, the dried hydrogel is used in the form of finely divided particles. The dried hydrogel particles may be formed by comminuting the dried hydrogel using methods known in the art, including, but not limited to, grinding, milling, or crushing with a mortar and pestle. The dried hydrogel may be applied to an anatomical site in a variety of ways, such as sprinkling or spraying, and may also be used to bond two anatomical sites together.

Kits

In one embodiment, the invention provides a kit comprising at least one oxidized dextran containing aldehyde groups and at least one aminodextran containing primary amine groups wherein the at least one oxidized dextran and the at least one aminodextran are unreacted; specifically, the at least one oxidized dextran and the at least one aminodextran are not crosslinked to form a hydrogel.

In one embodiment, the kit comprises at least one oxidized dextran and at least one aminodextran in the form of aqueous solutions or dispersions, as described above. Each of the aqueous solutions or dispersions may be contained in any suitable vessel, such as a vial or a syringe barrel.

In another embodiment, the kit comprises at least one oxidized dextran and at least one aminodextran in the form of finely divided powders, as described above. The powders may be contained in separate containers or they may be premixed and contained in a single container. The kit may also comprise a buffer solution for hydrating the powders.

In another embodiment, the kit comprises a dried hydrogel formed by reacting at least one oxidized dextran with at least one aminodextran, as described above. The dried hydrogel may be in the form of a film, finely divided particles, or other dried forms. The kit may further comprise a buffer for hydrating the dried hydrogel. The dried hydrogel particles may be contained in any suitable container.

Medical Applications

The dextran-based polymer tissue adhesive disclosed herein is particularly suitable for applications requiring low swell and slow degradation, for example sealing the dura, ophthalmic procedures, tissue repair, antiadhesive applications, drug delivery, and as a plug to seal a fistula or the punctum.

EXAMPLES

The present invention is further defined in the following Examples. It should be understood that these Examples, while indicating preferred embodiments of the invention, are given by way of illustration only. From the above discussion and the Examples that follow, one skilled in the art can ascertain the essential characteristics of this invention, and without departing from the spirit and scope thereof, can make various changes and modifications of the invention to adapt it to various uses and conditions.

A reference to "Aldrich" or a reference to "Sigma" means the said chemical or ingredient was obtained from Sigma-Aldrich, St. Louis, Mo.

All water used in these Examples was distilled-deionized water unless otherwise stated.

General Methods

Preparation of Oxidized Dextran

The following procedure was used to prepare an oxidized dextran, also referred to herein as dextran aldehyde, with about 50% aldehyde content conversion from dextran having a weight-average molecular weight of 8,500-11,500 Da. This dextran aldehyde is referred to herein as D10K-50. Other aldehyde conversions were obtained by varying the concentration of the periodate solution used. Likewise dextrans of other molecular weights were oxidized to provide the analogous oxidized dextran. Specifically, the following dextran aldehydes were prepared: weight-average molecular weight of 8.500-11,500 Da with an oxidation conversion of 50%, equivalent weight per aldehyde group of about 146 Da (D10K-50); weight-average molecular weight of 8,500-11,500 Da with an oxidation conversion of 65%, equivalent weight per aldehyde group of about 109 Da (D10K-65); weight-average molecular weight of 8.500-11,500 Da with an oxidation conversion of 20%, equivalent weight per aldehyde group of about 389 Da (D10K-20); weight-average molecular weight of 60,000-90,000 Da with an oxidation conversion of 50%, equivalent weight per aldehyde group of about 146 Da (D60K-50); weight-average molecular weight of 400-500 kDa with an oxidation conversion of 50%, equivalent weight per aldehyde group of about 146 Da (D450K-50); and weight-average molecular weight of approximately 2,000 kDa with an oxidation conversion of 46%, equivalent weight per aldehyde group of about 160 Da (D2000K-46).

Dextran (19.0 g; 0.12 mol saccharide rings; weight-average molecular weight of 8,500-11,500 Da; Sigma, product number D9260) was added to 170 g of water in a 500 mL round bottom flask. The mixture was stirred for 15 to 30 min to produce a solution; then a solution of 17.7 g (0.083 mol; mw=213.9) sodium periodate in 160 g of water was added to the dextran solution all at once. The mixture was stirred at room temperature for 5 h. After this time, the solution was removed from the round bottom flask, divided into four equal volumes and dispensed into 4 dialysis membrane tubes (MWCO=3500 Da). The tubes were dialyzed in distilled-deionized water for 4 days, during which time the water was changed twice daily. The aqueous solutions were removed from the dialysis tubes, placed in wide-mouth polyethylene containers and frozen using liquid nitrogen, and lyophilized to afford white, fluffy oxidized dextran.

The dialdehyde content in the resulting oxidized dextran was determined using the following procedure. The oxidized dextran (0.1250 g) was added to 10 mL of 0.25 M NaOH in a 250 mL Erlenmeyer flask. The mixture was gently swirled and then placed in a temperature-controlled sonicator bath at 40° C. for 5 min until all the material dissolved, giving a dark yellow solution. The sample was removed from the bath and the flask was cooled under cold tap water for 5 min. Then 15.00 mL of 0.25 M HCl was added to the solution, followed by the addition of 50 mL of water and 1 mL of 0.2% phenolphthalein solution. This solution was titrated with 0.25 M NaOH to an endpoint determined by a color change from yellow to purple/violet. The same titration was carried out on a sample of the starting dextran to afford a background aldehyde content. The dialdehyde content, also referred to herein as the oxidation conversion or the degree of oxidation, in the oxidized dextran sample was calculated using the following formula:

$$\text{Dialdehyde Content} = \frac{(Vb - Va)_s}{W_s/M} - \frac{(Vb - Va)_p}{W_p/M} \times 100\%.$$

Vb=total meq of base
Va=total meq of acid
W=dry sample weight (mg)
M=weight-average molecular weight of dextran repeat unit (162)

s=oxidized sample
p=original sample

Preparation of Aminodextran Having an Amine Substitution Level of 32% from Dextran Having a Weight-Average Molecular Weight of 60,000-90,000 Da (D60K-32 Amine)

Dextran aldehyde (D60K-50) with an oxidation conversion of 50%, equivalent weight per aldehyde group of about 146 Da, was prepared as described above using dextran having a weight-average molecular weight of 60,000-90,000 Da (Sigma, product number D3759). The dextran aldehyde (5.0 g) was dissolved in 500 mL of 0.1 M borate buffer, pH 11. The dextran aldehyde solution was added slowly over 5 h using an addition funnel to a basic solution of hexamethylene diamine in water (296 mL). The mixture was stirred at room temperature for 24 h. Then, sodium borohydride (4.14 g) was added, and the reaction mixture was stirred for 24 h. The reduction step was repeated with another addition of 4.14 g of sodium borohydride with stirring for another 24 h. The resulting solution was dialyzed in water using a 3500 MWCO dialysis membrane for 2 days, with 2 water exchanges, then lyophilized to dryness. The resulting aminodextran is referred to herein as D60K-32 amine.

$^1$H NMR (D$_2$O): 1.40 ppm (broad, integration 2.67), 1.52 ppm (broad, integration 1.16), 1.66 ppm (broad, integration 1.35), 2.97 ppm (broad, integration 1.05), 3.51-3.92 ppm (broad multiplet, integration 9.54), 4.98 ppm (broad, anomeric proton, integration 1).

The level of amine substitution was determined by $^1$H NMR to be 32% by calculating the ratio of the sum of the integrals at 1.40-1.66 ppm (NCH$_2$(C$\underline{H}_2$)$_4$CH$_2$NH$_2$) to the integral at 4.98 (anomeric protons) and comparing it to the expected ratio for a fully derivatized product. For example, for a fully derivatized product, a ratio of 16:1 is expected as the ratio of the sum of the integrals at 1.40-1.66 ppm (NCH$_2$(C$\underline{H}_2$)$_4$CH$_2$NH$_2$) to the integral at 4.98 (anomeric protons).

Elemental Analysis: % C, 45.53; % H, 7.34; % O, 40.99; % N, 4.46.

Preparation of Aminodextran Having an Amine Substitution Level of 46% from Dextran Having a Weight-Average Molecular Weight of 8,500-11,500 Daltons (D10K-46 Amine)

Dextran aldehyde (D10K-50) with an oxidation conversion of 50%, equivalent weight per aldehyde group of about 146 Da, was prepared as described above using dextran having a weight-average molecular weight of 8,500-11,500 Da. The dextran aldehyde (5.0 g) was dissolved in 500 mL of 0.1 M borate buffer, pH 11. The dextran aldehyde solution was added slowly over 5 h using a syringe pump to a basic solution of hexamethylene diamine (3.63 g, 0.031 mol) dissolved in 296 mL of water. The mixture was stirred at room temperature for 24 h. Then, sodium borohydride (4.14 g, 0.10 mol) was added, and the reaction mixture was stirred for 24 h at room temperature. The resulting solution was dialyzed in water using a 3500 MWCO dialysis membrane for 4 days, with 4 water exchanges, then lyophilized to dryness. The resulting aminodextran is referred to herein as D10K-46 amine.

$^1$H NMR (D$_2$O): 1.40 ppm, 1.54 ppm, 1.64 ppm (sum of integral of 1.40-1.64 ppm: 17.36), 2.3-2.96 ppm (broad, integral 11.16), 3.57-3.93 ppm (broad multiplet, integral 20.29), 4.98 ppm (broad, anomeric proton, integral 2.41).

The level of amine substitution was determined by $^1$H NMR to be 46% by calculating the ratio of the sum of the integrals at 1.40-1.64 ppm to the integral at 4.98 (anomeric protons) and comparing it to the expected ratio for a fully derivatized product (expected ratio of 16:1, as described above).

Elemental Analysis: % C, 9.42; % H, 7.91; % O, 35.30; % N, 6.48.

Preparation of Aminodextran Having an Amine Substitution Level of 38% from Dextran Having a Weight-Average Molecular Weight of 400-500 kDa (D450K-38 Amine)

Dextran aldehyde (D450K-50) with an oxidation conversion of 50%, equivalent weight per aldehyde group of about 146 Da, was prepared as described above using dextran having a weight-average molecular weight of 400-500 kDa (Sigma, product number D1037). The dextran aldehyde (5.0 g) was dissolved in 500 mL of 0.1 M borate buffer, pH 11. The dextran aldehyde solution was added slowly over 5 h using an addition funnel to a basic solution of hexamethylene diamine in 296 mL of water. The mixture was stirred at room temperature for 24 h. Then, sodium borohydride (4.14 g) was added, and the reaction mixture was stirred for 24 h. The reduction step was repeated with another addition of 4.14 g of sodium borohydride with stirring for another 24 h. The resulting solution was dialyzed in water using a 3500 MWCO dialysis membrane for 2 days, with 2 water exchanges, then lyophilized to dryness. The resulting aminodextran is referred to herein as D450K-38 amine.

$^1$H NMR (D$_2$O): 1.39 ppm, 1.49 ppm, 1.66 ppm (sum of integrals of 1.39-1.66 ppm is 6.09), 2.94 ppm (broad), 3.57-3.92 ppm (broad, integral 9.29), 4.96 ppm (broad, anomeric proton, integral 1.0).

The level of amine substitution was determined by $^1$H NMR to be 38% by calculating the ratio of the sum of the integrals at 1.40-1.64 ppm to the integral at 4.98 (anomeric protons) and comparing it to the expected ratio for a fully derivatized product (expected ratio of 16:1, as described above).

Preparation of Aminodextran Having an Amine Substitution Level of 36% from Dextran Having a Weight-Average Molecular Weight of Approximately 2,000 kDa (D2000K-36 Amine)

Dextran aldehyde (D2000K-46) with an oxidation conversion of 46%, equivalent weight per aldehyde group of about 160 Da, was prepared as described above using dextran having a weight-average molecular weight of approximately 2,000 kDa (Sigma, product number D5376). The dextran aldehyde (5.0 g) was dissolved in 500 mL of 0.1 M borate buffer, pH 11. The dextran aldehyde solution was added slowly over 5 h using an addition funnel to a basic solution of hexamethylene diamine in 296 mL of water. The mixture was stirred at room temperature for 24 h. Then, sodium borohydride (4.14 g) was added and the reaction mixture was stirred for 24 h. The reduction step was repeated with another addition of 4.14 g of sodium borohydride with stirring for another 24 h. The resulting solution was dialyzed in water using a 3500 MWCO dialysis membrane for 2 days, with 2 water exchanges, then lyophilized to dryness to yield 1.42 g of white solid. The resulting aminodextran is referred to herein as D2000K-36 amine.

$^1$H NMR (D$_2$O): 1.39 ppm (broad, integral 6.96), 1.51 ppm (broad, integral 3.56), 1.65 ppm (broad, integral 2.26), 2.9 ppm (broad, integral 3.39), 3.56-3.92 ppm (broad multiplet, integral 19.78), 4.96 ppm (broad, anomeric proton, integral 2.36).

The level of amine substitution was determined by $^1$H NMR to be 36% by calculating the ratio of the sum of the integrals at 1.39-1.65 ppm to the integral at 4.96 (anomeric protons) and comparing it to the expected ratio for a fully derivatized product (expected ratio of 16:1, as described above).

Preparation of Aminodextran Having an Amine Substitution Level of 13% from Dextran Having a Weight-Average Molecular Weight of 8,500-11,500 Daltons (D10K-13 Amine)

Dextran aldehyde (D10K-20) with an oxidation conversion of 20%, equivalent weight per aldehyde group of about 389 Da, was prepared as described above using dextran having a weight-average molecular weight of 8,500-11,500 Da. The dextran aldehyde (5.0 g) was dissolved in 500 mL of 0.1 M borate buffer, pH 11. The dextran aldehyde solution was added slowly over 5 h using a syringe pump to a basic solution of hexamethylene diamine (14.9 g, 0.12 mol) dissolved in 296 mL of water. The mixture was stirred at room temperature for 24 h. Then, sodium borohydride (4.14 g, 0.10 mol) was added, and the reaction mixture was stirred for 24 h at room temperature. The resulting solution was filtered using a TFF device (MWCO 1000, regenerated cellulose membrane). The solution was first concentrated to 1000 mL, then a 12× volume of waste was collected, and the resulting solution was lyophilized to dryness. The resulting aminodextran is referred to herein as D10K-13 amine.

$^1$H NMR (D$_2$O): 1.40 ppm, 1.54 ppm, 1.64 ppm (sum of integral of 1.40-1.64 ppm: 17.36), 2.3-2.96 ppm (broad, integral 11.16), 3.57-3.93 ppm (broad multiplet, integral 20.29), 4.98 ppm (broad, anomeric proton, integral 2.41).

The level of amine substitution was determined by $^1$H NMR to be 13% by calculating the ratio of the sum of the integrals at 1.40-1.64 ppm to the integral at 4.98 (anomeric protons) and comparing it to the expected ratio for a fully derivatized product (expected ratio of 16:1, as described above).

Preparation of Aminodextran Having an Amine Substitution Level of 41% from Dextran Having a Weight-Average Molecular Weight of 8,500-11,500 Daltons (D10K-41 Amine)

Dextran aldehyde (D10K-50) with an oxidation conversion of 50%, equivalent weight per aldehyde group of about 146 Da, was prepared as described above using dextran having a weight-average molecular weight of 8,500-11,500 Da. The dextran aldehyde (5 g) was dissolved in 500 mL of 0.1 M borate buffer, pH 11.0. The dextran aldehyde solution was added slowly over 5 hours using a syringe pump to a basic solution of hexamethylene diamine (36 g) dissolved in 296 mL of deionized water. The mixture was stirred at room temperature for 24 hours, after which time sodium borohydride (4 g) was added, and the reaction mixture was stirred for another 24 hours. Another aliquot of sodium borohydride (4 g) was added, and the reaction mixture was stirred for another 24 hours. The resulting solution was filtered using a Millipore Pellicon II TFF system (Millipore Corp., Billerica, Mass.) with a 1000 Da MWCO, regenerated cellulose membrane. The solution was first concentrated to a volume of 1000 mL, then a 12× volume of waste was collected, and then the resulting solution was lyophilized to dryness to yield the aminodextran, referred to herein as D10K-41 amine, as a white solid.

$^1$H NMR: $^1$H NMR (D$_2$O): 1.40 ppm, 1.54 ppm, 1.64 ppm (sum of integral of 1.40-1.64 ppm: 11.42), 2.3-2.96 ppm (broad, integral 7.7), 3.57-3.93 ppm (broad multiplet, integral 10.70), 4.98 ppm (broad, anomeric proton, integral 1.72).

The level of amine substitution was determined by $^1$H NMR to be 41% by calculating the ratio of the sum of the integrals at 1.40-1.64 ppm to the integral at 4.98 (anomeric protons) and comparing it to the expected ratio for a fully derivatized product (expected ratio of 16:1, as described above).

Examples 1-3

Preparation of Hydrogels by Reaction of an Aminodextran and a Dextran Aldehyde The following Examples demonstrate the preparation of hydrogels by reaction of an aminodextran and a dextran aldehyde. The gel time of the hydrogels was measured.

Into a small vial, 100 µL of an aqueous dextran aldehyde stock solution, as given in Table 1, was added. The vial was tilted and 100 µL of a 50 wt % aqueous D10K-46 amine solution was added with care taken not to mix the two solutions. A timer was started and the two solutions were stirred together with the wooden end of a cotton swab. The initial gel time was defined as the observation of increased viscosity, such that a string formed when the wooden stirring rod was pulled from the gel. The final gel time was defined as the second when stirring pulled the gel from the sides of the vial so that the gel could be removed as the wooden stirring rod was pulled from the vial.

The initial and final gel times are given in Table 1. The final gel times ranged from 10 to 34 sec, depending on the oxidation conversion and the concentration of the dextran aldehyde used.

TABLE 1

Gel Times of Hydrogels Prepared from Aminodextran and Dextran Aldehyde

| Example | Dextran Aldehyde Solution | Initial Gel Time (sec) | Final Gel Time (sec) |
|---|---|---|---|
| 1 | D10K-50 15 wt % | 15 | 21 |
| 2 | D10K-65 15 wt % | 4 | 10 |
| 3 | D10K-50 7.5 wt % | 28 | 34 |

Examples 4-6

In Vitro Biocompatibility Testing—Cytotoxicity

The purpose of these Examples was to demonstrate the safety of hydrogels resulting from the reaction of an aminodextran with a dextran aldehyde in an in vitro test.

The testing was done using NIH3T3 mouse fibroblast cell cultures according to ISO10993-5:1999. The NIH3T3 mouse fibroblast cells were obtained from the American Type Culture Collection (ATCC; Manassas, Va.) and were grown in Dulbecco's modified essential medium (DMEM), supplemented with 10% fetal calf serum.

NIH3T3 mouse fibroblast cell cultures were challenged with hydrogels made by combining equal volumes of an aqueous solution of a dextran aldehyde and an aqueous solution of an aminodextran, as shown in Table 2. Each hydrogel was placed in the bottom of a well in a polystyrene culture plate such that about 14 of the well bottoms were covered. The wells were then sterilized under UV light and seeded with 50,000-100,000 NIH3T3 cells.

The cells grew normally confluent and coated the well bottom, growing up to the edges of the hydrogels; however, they did not overgrow the hydrogels. These results, summarized in Table 2, demonstrate a lack of cytotoxicity of the hydrogels, as well as the lack of adhesion of cell cultures to the hydrogels.

TABLE 2

Cytotoxicity Results

| Example | Dextran Aldehyde Solution | Aminodextran Solution | Cytotoxicity |
|---|---|---|---|
| 4 | D10K-50 20 wt % | D450K-38 amine 20 wt % | nontoxic |
| 5 | D10K-50 20 wt % | D2000K-36 amine 20 wt % | nontoxic |
| 6 | D10K-50 25 wt % | D60K-32 amine 25 wt % | nontoxic |

Example 7

In Vitro Biocompatibility Testing—Inflammatory Response

The following Example demonstrate the non-inflammatory response produced by a hydrogel formed by reaction of a dextran aldehyde with an aminodextran in an in vitro test using J774 Macrophage.

The testing was done using J774 Macrophage cultures according to ISO10993-5:1999. The J774 Macrophage cells were obtained from ATCC and were grown in DMEM supplemented with 10% fetal bovine serum.

A J774 mouse peritoneal macrophage cell culture was challenged with a hydrogel made by combining equal volumes of an aqueous solution of D10K-46 dextran amine (25 wt %) and an aqueous solution of D10K-50 dextran aldehyde (20 wt %). The hydrogel was placed on the bottom of a well in a polystyrene culture plate such that about ¼ of the well bottom was covered. The well was then sterilized under UV light and seeded with J774 cells. The cell culture was then analyzed for TNF-α, an indicator of inflammatory response, using an ELISA assay, as described by Lara et al. (*Journal of Dental Research* 82(6):460-465, 2003). The TNF-α titer was similar to the negative control (a blank well), indicating the noninflammatory nature of the hydrogel.

Examples 8-13

In-Vitro Burst Testing of a Sealed Scalpel Incision

The following Examples demonstrate the burst strength of a seal made with various hydrogels of an incision made in swine uterine horn.

A syringe pump system was used to measure the burst strength of a seal of an incision made in a section of swine uterine horn. The syringe pump (Model No. 22, Harvard Apparatus, Holliston, Mass.) was modified to be equipped with two 30 mL syringes, which were connected together through a "Y" junction. Water was pumped through a single piece of Tygon® R-36 tubing (0.6 cm diameter) and through a pressure gauge (Model PDG 5000L, Omega Engineering, Stamford, Conn.).

An approximately 12.5 cm section of clean swine uterine horn, obtained from a local abattoir, was fitted on one end with a metal plug with a feed line fitting for water feed from the syringe pump and on the other end with a metal plug with a threaded hole which could be sealed with a machine screw. The plugs were held in place with nylon ties around the outside of the uterine horn. An incision was made through the uterine horn wall into the interior by puncturing with a Bard Parker™ surgical blade handle 5 (obtained from BD Surgical Products, Franklin Lakes, N.J.), fitted with a #15 surgical blade. The incision on the outside of the uterine horn was wider than the scalpel blade (typically 4-5 mm) while the hole through the inside wall was about 3 mm (about equal to the blade). This size incision mimics the distance between the interrupted sutures if an intestine were to be cut and later sutured. The uterine horn was filled with water containing a purple dye via the syringe pump until water began to leak from the open hole in the end plug and also from the scalpel puncture in the uterine horn wall. The pump was then turned off and the end plug was sealed with the machine screw. The scalpel incision site was blotted dry using a paper towel.

The dextran aldehyde and aminodextran solutions were prepared in water. The two solutions were applied to the incision using a double barrel syringe (Mixpac Systems AG (Rotkreuz, Switzerland) fitted with a 16 step static mixer (Mixpac Systems AG). After the application, the adhesive was allowed to cure at room temperature for no longer than 2 min.

Burst pressure testing, also referred to herein as leak pressure testing, was done by pressurizing the sealed uterine horn with water from the syringe pump at a flow rate of 11 mL/min until the bioadhesive seal began to leak, at which point the pressure was recorded. Adhesive failure was attributed when the water leaked under the seal between the hydrogel and the tissue surface. Cohesive failure was attributed when the water penetrated and leaked through the hydrogel itself. Burst pressure testing was also done on the unsealed uterine horn and the leak pressure was less than 10 mm of mercury (Hg) (less than 1.3 kPa).

The results of the burst testing are summarized in Table 3. The results demonstrate the hydrogels formed by reaction of various dextran aldehyde and aminodextran solutions were able to seal the incision in the swine uterine horn.

TABLE 3

Burst Pressure Testing Results

| Example | Dextran Aldehyde Solution | Aminodextran Solution | Ave Burst Pressure, mm Hg | Standard Deviation Burst Pressure, mm Hg |
|---|---|---|---|---|
| 8 | D10K-50 17 wt % | D60K-32 amine 20 wt % | 52.7 (7.0 kPa) | 17.1 (2.3 kPa) |
| 9 | D10K-50 17 wt % | D60K-32 amine 10 wt % | 45.0 (6.0 kPa) | 31.8 (4.2 kPa) |
| 10 | D10K-50 10 wt % | D60K-32 amine 20 wt % | 46.9 (6.2 kPa) | 19.0 (2.5 kPa) |
| 11 | D10K-50 20 wt % | D10K-46 amine 40 wt % | 39.1 (5.2 kPa) | 13.0 (1.7 kPa) |
| 12 | D10K-80 20 wt % | D10K-13 amine 20 wt % | 64.6 (8.6 kPa) | 9.3 (1.2 kPa) |
| 13 | D10K-80 20 wt % | D10K-41 amine 40 wt % | 61.5 (8.2 kPa) | 22.7 (3.0 kPa) |

Examples 14-16

In Vitro Degradation of Hydrogels

The following Examples demonstrate that the hydrogels formed by reaction of an aminodextran with a dextran aldehyde have low swell and persist for prolonged periods of time in vitro.

The hydrogel samples were prepared by mixing equal volumes of an aqueous solution of a dextran aldehyde and an aqueous solution of an aminodextran, as shown in Table 4. After the hydrogels cured, the samples were weighed and placed inside jars containing phosphate-buffered saline (PBS). The jars were placed inside a temperature-controlled shaker set at 80 rpm and 37° C. The samples were removed from the jars at various times, blotted to remove excess solution, and weighed. Then, the samples were returned to the jars.

The results are summarized in Table 4. The percent swell reported in the table is the weight of the hydrogel at the specified time divided by the initial weight of the hydrogel, multiplied by 100. All of the hydrogels were still present after 13 days (312 h). The results indicate that the hydrogels have low swell and persist for long periods of time.

TABLE 4

Results of In Vitro Degradation of Hydrogels

| | Dextran Aldehyde | Aminodextran | % Swell | | | |
|---|---|---|---|---|---|---|
| Example | Solution | Solution | 2 h | 24 h | 120 h | 312 h |
| 14 | D10K-50 20 wt % | D450K-38 amine 20 wt % | 41 | 28 | 23 | 9 |
| 15 | D10K-50 20 wt % | D10K-46 amine 20 wt % | 106 | 48 | 35 | 27 |
| 16 | D10K-50 25 wt % | D60K-32 amine 20 wt % | 98 | 44 | 29 | 23 |

Example 17

In Vitro Testing of Dextran Amine for Inhibition of *E. coli* Growth

The following Example demonstrates the antimicrobial activity of dextran amine by testing inhibition of *E. coli* growth.

A suspension culture of *E. coli* (strain K12, ATCC No. 25257) from American Type Culture Collection (ATCC; Manassas, Va.) was prepared by seeding an individual colony into 4 mL of Luria Broth (obtained from ATCC). The culture was incubated in a shaker overnight at 37° C. to allow the culture to reach the saturation point of cell growth. The concentration of *E. coli* in the saturated overnight culture was approximately $1 \times 10^9$ cells/mL. The saturated overnight culture (10 µL) was then seeded into 4 mL of Luria Broth, and the desired amount of a dextran amine was added, as indicated in Table 5. The culture was incubated in a shaker overnight at 37° C. Following the incubation, bacterial growth was quantified by measuring the optical density of the culture at 600 nm using a spectrophotometer. This method for determining in vitro antimicrobial activity has been shown to correlate with in vivo antimicrobial activity (Lee S H et al., *Journal of Pharmacy and Pharmacology* 2003 April; 55:559-66). The results are summarized in Table 5. The bacteriostatically effective amount of dextran amine, i.e., the amount of the dextran amine that produced a 0.5 log decrease in bacterial growth, is also given in the Table. The bacteriostatically effective amount of the dextran amine was estimated from a plot of the log of bacterial growth (cells/mL) versus the volume of dextran amine solution added to the culture medium.

TABLE 5

Inhibition of *E. coli* Growth by Dextran Amines

| Example | Dextran amine | Volume Added (µL) | Bacterial Growth (cells/mL) | Bacteriostatically Effective Amount (mg/mL) |
|---|---|---|---|---|
| 17 | D10K-41 amine 10 wt % | 0 | $1.0 \times 10^9$ | ≥5 |
| | | 20 | $7.1 \times 10^8$ | |
| | | 50 | $1.7 \times 10^8$ | |

What is claimed is:

1. A method for applying a coating to an anatomical site on tissue of a living organism comprising:
   applying to the site
   a) at least one dextran that has been derivatized to provide at least one aminodextran that contains primary amine groups, said at least one dextran having a weight-average molecular weight of about 1,000 to about 1,000,000 Daltons, said at least one aminodextran having an amine substitution level of about 5% to about 65%; followed by
   b) at least one dextran that has been oxidized to provide at least one oxidized dextran containing aldehyde groups, said at least one dextran having a weight-average molecular weight of about 1,000 to about 1,000,000 Daltons, said at least one oxidized dextran having an equivalent weight per aldehyde group of about 65 to about 1500 Daltons;
   or applying (b) followed by (a) and mixing (a) and (b) on the site;
   or premixing (a) and (b) and applying the resulting mixture to the site.

2. The method according to claim 1 wherein the aminodextran is a first aqueous solution or dispersion and the oxidized dextran a second aqueous solution or dispersion.

3. The method according to claim 2 wherein the first aqueous solution or dispersion contains the aminodextran at a concentration of about 5% to about 70% by weight relative to the total weight of the solution or dispersion.

4. The method according to claim 2 wherein the second aqueous solution or dispersion contains the oxidized dextran at a concentration of about 5% to about 50% by weight relative to the total weight of the solution or dispersion.

5. The method according to claim 1 wherein the aminodextran and the oxidized dextran are finely divided powders.

6. The method according to claim 1 wherein the equivalent weight per aldehyde group of the oxidized dextran is about 90 to about 1500 Daltons.

7. A method for bonding at least two anatomical sites together comprising:
   applying to at least one of the at least two anatomical sites:
   a) at least one dextran that has been derivatized to provide at least one aminodextran that contains primary amine groups, said at least one dextran having a weight-average molecular weight of about 1,000 to about 1,000,000 Daltons, said at least one aminodextran having an amine substitution level of about 5% to about 65%; followed by
   b) at least one dextran that has been oxidized to provide at least one oxidized dextran containing aldehyde groups, said at least one dextran having a weight-average molecular weight of about 1,000 to about 1,000,000 Daltons, said at least one oxidized dextran having an equivalent weight per aldehyde group of about 65 to about 1500 Daltons; or alternatively, applying (b) followed by (a) and mixing (a) and (b) on the at least one site, or alternatively, premixing (a) and (b) and applying the resulting mixture to the at least one site; and contacting the at least two anatomical sites together.

8. The method according to claim 7 wherein the aminodextran is a first aqueous solution or dispersion and the oxidized dextran a second aqueous solution or dispersion.

9. The method according to claim 8 wherein the first aqueous solution or dispersion contains the aminodextran at a concentration of about 5% to about 70% by weight relative to the total weight of the solution or dispersion.

10. The method according to claim 8 wherein the second aqueous solution or dispersion contains the oxidized dextran at a concentration of about 5% to about 50% by weight relative to the total weight of the solution or dispersion.

11. The method according to claim 7 wherein the aminodextran and the oxidized dextran are finely divided powders.

12. The method according to claim 7 wherein the equivalent weight per aldehyde group of the oxidized dextran is about 90 to about 1500 Daltons.

* * * * *